United States Patent
van Doormalen

(10) Patent No.: US 10,206,354 B2
(45) Date of Patent: Feb. 19, 2019

(54) LEEK VARIETY NUN 50215 LEL

(71) Applicant: Nunhems B.V., AB Nunhem (NL)

(72) Inventor: Antonius Joseph Gerardus van Doormalen, Meijel (NL)

(73) Assignee: NUNHEMS B.V., Nunhem (NL)

( * ) Notice: Subject to any disclaimer, the term of this patent is extended or adjusted under 35 U.S.C. 154(b) by 0 days.

(21) Appl. No.: 15/903,691

(22) Filed: Feb. 23, 2018

(65) Prior Publication Data

US 2018/0184611 A1    Jul. 5, 2018

Related U.S. Application Data

(60) Provisional application No. 62/541,127, filed on Aug. 4, 2017, provisional application No. 62/516,835, filed on Jun. 8, 2017.

(51) Int. Cl.
  *A01H 5/10*  (2018.01)
  *A01H 5/12*  (2018.01)
  *A01H 6/04*  (2018.01)

(52) U.S. Cl.
  CPC .................. *A01H 5/10* (2013.01); *A01H 5/12* (2013.01); *A01H 6/04* (2018.05); *A01H 6/045* (2018.05)

(58) Field of Classification Search
  None
  See application file for complete search history.

(56) References Cited

U.S. PATENT DOCUMENTS

2013/0202775 A1 *  8/2013  Van Doormalen ...... A01H 5/12
                                                    426/635

FOREIGN PATENT DOCUMENTS

WO    2013182646 A1    12/2013
WO    2014076249 A1    5/2014

OTHER PUBLICATIONS

Ren, Yan, et al., Shoot regeneration and ploidy variation in tissue culture of honeydew melon (*Cucumis melo* L. inodorus), In Vitro Cell.Dev.Biol.—Plant, 2013, pp. 223-229, vol. 49.
Guidelines for the conduct of tests for distinctness, uniformity and stability, UPOV (International Union for the Protection of New Varieties and Plants), Apr. 9, 2008, TG/85/7 http://www.upov.int/edocs/tgdocs/en/tg085.pdf.
Colijn-Hooymans, C.M., et al., Competence for regeneration of cucumber cotyledons is restricted to specific developmental stages, Plant Cell, Tissue and Organ Culture, 1994, pp. 211-217, vol. 39.
Vos, Pieter, et al., AFLP: a new technique for DNA fingerprinting, Nucleic Acids Research, 1995, pp. 4407-4414, vol. 23 No. 21.
Brotman, Y, et al., Resistance gene homologues in melon are linked to genetic loci conferring disease and pest resistance, Theor Appl Genet, 2002, pp. 1055-1063, vol. 104.
Parvathaneni, Rajiv Krishna, et al., Fingerprinting in Cucumber and Melon (*Cucumis* spp.) Genotypes Using Morphological and ISSR Markers, J. Crop Sci. Biotech., Mar. 2011, pp. 39-43, vol. 14, No. 1.
Wijnker et al., Hybrid recreation by reverse breeding in *Arabidopsis thaliana*, Nature Protocols, 2014, pp. 761-772, vol. 9.

* cited by examiner

*Primary Examiner* — Vinod Kumar
(74) *Attorney, Agent, or Firm* — Arent Fox LLP

(57) ABSTRACT

The invention provides a new and distinct hybrid variety of Leek, NUN 50215 LEL as well as seeds and plants and leaves or shafts thereof.

19 Claims, No Drawings

LEEK VARIETY NUN 50215 LEL

CROSS-REFERENCE TO RELATED APPLICATIONS

The present application claims the benefit of U.S. patent application Ser. No. 62/516,835, filed 2017 Jun. 8, and U.S. patent application Ser. No. 62/541,127, filed 2017 Aug. 4, each of which is incorporated herein by reference in its entirety.

FIELD OF THE INVENTION

The present invention relates to the field of plant breeding and, more specifically, to the development of NUN 50215 LEL (also designated as NUN 50215 or NUN 50215 F1 or NUN 50215 hybrid). The invention further relates to vegetative reproductions of NUN 50215 LEL, methods for tissue culture of NUN 50215 LEL and regenerating a plant from such a tissue culture and also to phenotypic variants of NUN 50215 LEL.

The goal of vegetable breeding is to combine various desirable traits in a single variety/hybrid. Such desirable traits may include greater yield, resistance to diseases, insects or other pests, tolerance to heat and drought, better agronomic quality, higher nutritional value, enhanced growth rate and improved leaf properties.

Breeding techniques take advantage of a plant's method of pollination. There are two general methods of pollination: a plant self-pollinates if pollen from one flower is transferred to the same or another flower of the same genotype. A plant cross-pollinates if pollen comes to it from a flower of a different genotype.

Plants that have been self-pollinated and selected for (uniform) type over many generations become homozygous at almost all gene loci and produce a uniform population of true breeding progeny of homozygous plants. A cross between two such homozygous plants of different lines produces a uniform population of hybrid plants that are heterozygous for many gene loci. The extent of heterozygosity in the hybrid is a function of the genetic distance between the parents. Conversely, a cross of two plants each heterozygous at a number of loci produces a segregating population of hybrid plants that differ genetically and are not uniform. The resulting non-uniformity makes performance unpredictable.

The development of uniform varieties requires the development of homozygous inbred plants, the crossing of these inbred plants to make hybrids, and the evaluation of the hybrids resulting from the crosses. Pedigree breeding and recurrent selection are examples of breeding methods that have been used to develop inbred plants from breeding populations. Those breeding methods combine the genetic backgrounds from two or more plants or various other broad-based sources into breeding pools from which new lines are developed by selfing and selection of desired phenotypes. The new plants are evaluated to determine which have commercial potential. One crop species which has been subject to such breeding programs and is of particular value is leek.

Leek (*Allium ampeloprasum* var. *porrum* (L.) or *Allium porrum*) belongs to the Alliceae family and is used as a crop in diverse countries. Most of the commercially available leek varieties are leek hybrid plants. These leek hybrid plants are plants produced by crossing a selected leek population with another selected leek population. The leek hybrid plants provide advantages over open pollinated crossbreds, such as uniformity, vitality and disease tolerance, resulting in an increased use of leek hybrids in commercial leek productions. Leek hybrid plants are generally produced by a technique designated in the art as "nuclear male sterility". Nuclear male sterility is a form of male sterility wherein the genetic factor responsible for the observed sterility is encoded by the nuclear genome. The term "Male sterility" indicates that a plant has no fertile pollen and, because of this, the male sterile plant is incapable of self-pollination.

Rather than forming a tight bulb like the onion, the leek produces a long cylinder of bundled leaf sheaths which are generally blanched by pushing soil around them (trenching). They are often sold as small seedlings in flats which are started off early in greenhouses, to be planted out as weather permits. Once established in the field or garden, leeks are hardy; many varieties can be left in the ground during the winter to be harvested as needed.

Leek cultivars can mainly be divided in three types: Summer leek, Autumn leek and Winter leek. Summer leek is fast growing leek, leaf color is green. Harvest period is early summer to late summer/beginning of autumn. Autumn leek is medium fast to medium slow growing leek. Leaf color is dark green to blue-green. Varieties are more tolerant to low temperatures. Most genotypes in this type have a shorter shaft compared to the summer leek. Harvest period is early autumn, autumn, beginning of winter. Winter leek is slow growing leek. Foliage color is dark green mostly blue-green; varieties are tolerant to cold and to frost to some extent. Winter hardiness is good. Shafts are rather short. Harvest period is end of autumn, winter until early spring (just before bolting starts). The edible portions of the leek are the white base of the leaves (above the roots and stem base), the light green parts, and to a lesser extent the dark green parts of the leaves. One of the most popular uses is for adding flavor to stock. The use of a type of leek depends on the growth habit of said leek and a customer's preference for shape of leaves/the plant, and color.

While breeding efforts to date have provided a number of useful leek lines with beneficial traits, there remains a great need in the art for new varieties with further improved traits. Such plants would benefit farmers and consumers alike by improving crop yields and/or quality.

SUMMARY OF THE INVENTION

In an aspect of the invention, a seed of Leek variety NUN 50215 LEL is provided, wherein a representative sample of said seed will be deposited under Accession Number NCIMB 42794. The invention also provides for a plurality of seeds of NUN 50215 LEL. The Leek seed of NUN 50215 LEL may be provided as an essentially homogeneous population of Leek seed. Therefore, seed of the invention may be defined as forming at least about 97% of the total seed, including at least about 98%, 99% or more of the seed. The population of seed of NUN 50215 LEL may be particularly defined as being essentially free from other seed. The seed population may be grown into plants to provide an essentially homogeneous population of Leek plants according to the invention.

Also encompassed is a plant grown from a seed of Leek variety NUN 50215 LEL and a plant part thereof. In another aspect the invention provides for a hybrid variety of Leek called NUN 50215 LEL. The invention also provides for a progeny of NUN 50215 LEL. Especially, a plant or a progeny retaining all or all but one, two or three of the "distinguishing characteristics" or all or all but one, two or three of the "morphological and physiological characteristics" of NUN 50215 LEL referred to herein, is encompassed herein as well as methods for producing that plant or progeny.

In one aspect, a plant or a progeny of the invention have all the physiological and morphological characteristics of variety NUN 50215 LEL when grown under the same environmental conditions. In another aspect such a plant or such progeny have all or all but one, two or three of the physiological and morphological characteristics of NUN 50215 LEL when measured under the same environmental conditions and evaluated at significance levels of 1%, 5% or 10% significance (which can also be expressed as a p-value) wherein a representative sample of seed of variety NUN 50215 LEL has been deposited under Accession Number NCIMB 42794. In a second aspect, a plant or a progeny of the invention have all the physiological and morphological characteristics of variety NUN 50215 LEL when grown under the same environmental conditions. In another aspect such a plant or such progeny have all or all but one, two or three of the physiological and morphological characteristics as listed in Table 1 and/or 2 for variety NUN 50215 LEL when measured under the same environmental conditions and evaluated at significance levels of 1%, 5% or 10% significance.

In another aspect a plant of NUN 50215 LEL or said progeny plants has 7, 8, or more or all of the distinguishing characteristics: 1) Average plant height; 2) Shaft bulb formation type; 3) Shaft narrowing type; 4) Leaf blade bending; 5) Average leaf blade length; 6) Average leaf angle; and 7) Leaf blade color. NUN 50215 LEL is a long shafted leek.

Also a plant part obtained from variety NUN 50215 LEL is provided, wherein said plant part is selected from the group consisting of: a leaf, a harvested leaf, a part of a leaf, a shaft, a harvested shaft, a part of a shaft, a fruit, a harvested fruit, a part of a fruit, pollen, an ovule, a cell, a petiole, a shoot or a part thereof, a stem or a part thereof, a root or a part thereof, a root tip, a cutting, a seed, a part of a seed, seed coat or another maternal tissue which is part of a seed grown on said varieties, hypocotyl, cotyledon, a scion, a stock, a rootstock, a pistil, an anther, and a flower or a part thereof. Leaves and shafts are particularly important plant parts. In a further embodiment, the plant part obtained from variety NUN 50215 LEL is a cell, optionally a cell in a cell or tissue culture. That cell may be grown into a plant of NUN 50215 LEL.

The invention also provides a cell culture of NUN 50215 LEL and a plant regenerated from NUN 50215 LEL, which plant has all the characteristics of NUN 50215 LEL when grown under the same environmental conditions, as well as methods for regenerating NUN 50215 LEL. Alternatively, a regenerated plant may have one characteristic that is different from NUN 50215 LEL.

Further, a vegetatively propagated plant of variety NUN 50215 LEL is provided having all or all but one, two or three of the morphological and physiological characteristics NUN 50215 LEL when grown under the same environmental conditions.

Further, a Leek shaft or leaf produced on a plant grown from a seed of NUN 50215 LEL is provided.

In still another aspect, a seed growing or grown on a plant of NUN 50215 LEL is provided (i.e. produced after pollination of the flower of NUN 50215 LEL).

Definitions

All patent and non-patent documents cited herein are incorporated by reference in their entirety "Leek" refers herein to plants of the species *Allium ampeloprasum*. The most commonly eaten parts of Leek are the shaft and leaves.

"Cultivated leek" refers to plants of *Allium ampeloprasum* L, i.e. varieties, breeding lines or cultivars of the species *Allium ampeloprasum* L, cultivated by humans and having good agronomic characteristics; preferably such plants are not "wild plants", i.e. plants which generally have much poorer yields and poorer agronomic characteristics than cultivated plants and e.g. grow naturally in wild populations. "Wild plants" include for example ecotypes, PI (Plant Introduction) lines, landraces or wild accessions or wild relatives of a species.

The terms "Leek NUN 50215 LEL", "NUN 50215 LEL", "NUN 50215", "NUN 50215 F1", "50215 LEL" or "Leek 50215" are used interchangeably herein and refer to a Leek plant of variety NUN 50215 LEL, representative seed of which having been deposited under Accession Number NCIMB 42794.

A "seed of NUN 50215 LEL" refers to a Leek seed which can be grown into a plant of NUN 50215 LEL wherein a representative sample of viable seed of NUN 50215 LEL has been deposited under Accession Number NCIMB 42794. A seed can be in any stage of maturity, for example a mature, viable seed, or an immature, non-viable seed. A seed comprises an embryo and maternal tissues.

An "embryo of NUN 50215 LEL" refers to an "F1 hybrid embryo" as present in a seed of NUN 50215 LEL, a representative sample of said seed of NUN 50215 LEL having been deposited under Accession Number NCIMB 42794.

A "seed grown on NUN 50215 LEL" refers to a seed grown on a mature plant of NUN 50215 LEL or inside a fruit of NUN 50215 LEL. The "seed grown on NUN 50215 LEL" contains tissues and DNA of the maternal parent, NUN 50215 LEL. The "seed grown on NUN 50215 LEL" contains an F2 embryo. When said seed is planted, it grows into a first generation progeny plant of NUN 50215 LEL.

"Tissue culture" or "cell culture" refers to a composition comprising isolated cells of the same or a different type or a collection of such cells organized into parts of a plant. Tissue culture of various tissues of cucumber and regeneration of plants therefrom is well known and widely published (see, e.g., Ren et al., In Vitro Cell.Dev.Biol.-Plant (2013) 49:223-229; Colijn-Hooymans (1994), Plant Cell, Tissue and Organ Culture 39: 211-2177). Similarly, the skilled person is well-aware how to prepare a "tissue culture" or "cell culture".

"UPOV descriptors" are the plant variety descriptors described for leek in the "Guidelines for the Conduct of Tests for Distinctness, Uniformity and Stability, TG/85/7 (Geneva 2008), as published by UPOV (International Union for the Protection of New Varieties and Plants, available on the world wide web at upov.int) and which can be downloaded from the world wide web at upov.int/edocs/tgdocs/en/tg085.pdf and is herein incorporated by reference in its entirety.

"RHS" refers to the Royal Horticultural Society of England which publishes an official botanical color chart quantitatively identifying colors according to a defined numbering system. The chart may be purchased from Royal Horticulture Society Enterprise Ltd RHS Garden; Wisley, Woking; Surrey GU236QB, UK, e.g., the RHS color chart: 2007 (The Royal Horticultural Society, charity No: 222879, PO Box 313 London SW1P2PE.

As used herein and except as otherwise indicated, the term "plant" includes the whole plant or any part thereof, preferably having the same genetic makeup as the plant from which it is obtained, such as a plant organ (e.g. harvested or non-harvested leaves or shafts), a plant cell, a plant protoplast, a plant cell tissue culture or a tissue culture from which a whole plant can be regenerated, a plant cell that is intact in a plant, a clone, a micropropagation, plant callus, a plant cell clump, a plant transplant, a vegetative propagation, a seedling, or parts of a plant (e.g. harvested tissues or organs), such as a leaf, a part of a leaf, a shaft, a part of shaft, a fruit, a harvested fruit, a part of a fruit, a leaf, pollen, an ovule, an embryo, a petiole, a shoot or a part thereof, a stem or a part thereof, a root or a part thereof, a root tip, a cutting, a seed, a part of a seed, seed coat or another maternal tissue which is part of a seed grown on a variety of the invention, hypocotyl, cotyledon, a scion, a graft, a stock, a rootstock, a pistil, an anther, and a flower or parts of any of these and the like. Also any developmental stage is included, such as seedlings, cuttings prior or after rooting, mature plants or leaves. Alternatively, a plant part may also include a plant seed which comprises one or two sets of chromosomes derived from the parent plant, e.g. from NUN 50215 LEL. An F2 progeny produced from self-pollination of NUN 50215 LEL will thus comprise two sets of chromosomes derived from NUN 50215 LEL, while an F2 progeny derived from cross-fertilization of NUN 50215 LEL will comprise only one set of chromosomes from NUN 50215 LEL and the other set of chromosomes from the other parent.

"Harvested plant material" refers herein to plant parts (e.g. shafts or leaves detached from the whole plant) which have been collected for further storage and/or further use.

"REFERENCE VARIETY" refers to the variety Krypton from company Nunhems, which has been planted in a trial together with NUN 50215 LEL. Descriptors/characteristics of NUN 50215 LEL were compared to the descriptors of REFERENCE VARIETY.

A plant having "all the physiological and morphological characteristics" of a referred-to-plant means a plant showing the physiological and morphological characteristics of the referred-to-plant when grown under the same environmental conditions, preferably in the same experiment; the referred-to-plant can be a plant from which it was derived, e.g. the progenitor plant, the parent, the recurrent parent, the plant used for tissue- or cell culture, etc. A physiological or morphological characteristic can be a numerical characteristic or a non-numerical characteristic. In one aspect, a plant has "all but one, two or three of the physiological and morphological characteristics" of a referred-to-plant, or "all the physiological and morphological characteristics" of Table 1 and/or 2 or "all or all but one, two or three of the physiological and morphological characteristics" of Table 1 and/or 2.

The physiological and/or morphological characteristics mentioned above are commonly evaluated at significance levels of 1%, 5% or 10% if they are numerical, or for having an identical degree (or type) if not numerical, if measured under the same environmental conditions. For example, a progeny plant or a Single Locus Converted plant or a mutated plant of NUN 50215 LEL may have one or more (or all) of the essential physiological and/or morphological characteristics of said variety listed in Table 1 and/or 2, as determined at the 5% significance level (i.e. p<0.05) when grown under the same environmental conditions.

"Distinguishing characteristics" or "distinguishing morphological and/or physiological characteristics" refers herein to the characteristics which distinguish (i.e. are different) between the new variety and other Leek varieties, such as the Reference Variety, when grown under the same environmental conditions. The distinguishing characteristics between NUN 50215 LEL and Reference Variety are described elsewhere herein and also can be seen in Table 1 and/or Table 2. When comparing NUN 50215 LEL with different varieties, the distinguishing characteristics will be different. In one aspect, the distinguishing characteristics may therefore include at least one, two, three or more (or all) of the characteristics listed in Table 1 and/or 2 and/or 3. All numerical distinguishing characteristics are statistically significantly different at p<0.05 between NUN 50215 LEL and the other variety, e.g. Reference Variety.

NUN 50215 LEL has the following distinguishing characteristics when compared to the Reference Variety: 1) Average plant height; 2) Shaft bulb formation type; 3) Shaft narrowing type; 4) Leaf blade bending; 5) Average leaf blade length; 6) Average leaf angle; and 7) Leaf blade color. This can be seen in a.m. Table 1, where the USDA characteristics of NUN 50215 LEL are compared to the characteristics of Reference Variety, when grown under the same environmental conditions Thus, a Leek plant "comprising the distinguishing characteristics of NUN 50215 LEL (such as a progeny plant) refers herein to a plant which does not differ significantly from said variety in the distinguishing characteristics above. Therefore in one aspect a plant (such as a progeny plant of NUN 50215 LEL) is provided which does not differ significantly from NUN 50215 LEL in the distinguishing characteristics above.

Similarity and differences between two different plant lines or varieties can be determined by comparing the number of morphological and/or physiological characteristics (e.g. the characteristics as listed in Table 1 and/or 2) that are the same (i.e. statistically not significantly different) or that are different (i.e. statistically significantly different) between the two plant lines or varieties when grown under the same environmental conditions. A numerical characteristic is considered to be "the same" when the value for a numeric characteristic is not significantly different at the 1% (p<0.01) or 5% (p<0.05) significance level, using one way Analysis of variance (ANOVA), a standard method known to the skilled person. Non-numerical or "degree" or "type" characteristic are considered "the same" when the values have the same "degree" or "type" when scored using USDA and/or UPOV descriptors, if the plants are grown under the same environmental conditions.

As used herein, the term "variety", "cultivated Leek" or "cultivar" means a plant grouping within a single botanical taxon of the lowest known rank, which grouping, irrespective of whether the conditions for the grant of a breeder's right are fully met, can be defined by the expression of the characteristics resulting from a given genotype or combination of genotypes, distinguished from any other plant grouping by the expression of at least one of the said characteristics and considered as a unit with regard to its suitability for being propagated unchanged.

A "plant line" is for example a breeding line which can be used to develop one or more varieties. A breeding line is typically highly homozygous.

"Hybrid variety" or "F1 hybrid" refers to the seeds harvested from crossing two inbred (nearly homozygous) parental lines. For example, the female parent is pollinated with pollen of the male parent to produce hybrid (F1) seeds on the female parent.

"Regeneration" refers to the development of a plant from cell culture or tissue culture or vegetative propagation.

"Vegetative propagation", "vegetative reproduction" or "clonal propagation" are used interchangeably herein and mean a method of taking a part of a plant and allowing that plant part to form at least roots, and also refer to the plant or plantlet obtained by that method. Optionally, the vegetative propagation is grown into a mature plant. The skilled person is aware of what plant parts are suitable for use in the method.

"Selfing" refers to self-pollination of a plant, i.e., the transfer of pollen from the anther to the stigma of the same plant.

"Crossing" refers to the mating of two parent plants. The term encompasses "cross-pollination" and "selfing".

"Cross-pollination" refers to the fertilization by the union of two gametes from different plants.

"Yield" means the total weight of all Leek leaves or shafts harvested per hectare of a particular line or variety. It is understood that "yield" expressed as weight of all Leek leaves or shafts harvested per hectare can be obtained by multiplying the number of plants per hectare times the "yield per plant". "Marketable yield" means the total weight of all marketable Leek leaves or shafts, especially leaves or shafts that is not damaged or diseased, harvested per hectare of a particular line or variety.

As used herein, the terms "resistance" and "tolerance" are used interchangeably to describe plants that show no symptoms or significantly reduced symptoms to a specified biotic pest, pathogen, abiotic influence or environmental condition compared to a susceptible plant. These terms are optionally also used to describe plants showing some symptoms but that are still able to produce marketable product with an acceptable yield.

The term "traditional breeding techniques" encompasses herein crossing, selfing, selection, doubled haploid production, embryo rescue, protoplast fusion, marker assisted selection, mutation breeding etc. as known to the breeder (i.e. methods other than genetic modification/transformation/transgenic methods), by which, for example, a genetically heritable trait can be transferred from one Leek line or variety to another. It optionally includes epigenetic modifications.

"Backcrossing" is a traditional breeding technique used to introduce a trait into a plant line or variety. The plant containing the trait is called the donor plant and the plant into which the trait is transferred is called the recurrent parent. An initial cross is made between the donor parent and the recurrent parent to produce a progeny plant. Progeny plants which have the trait are then crossed to the recurrent parent. After several generations of backcrossing and/or selfing the recurrent parent comprises the trait of the donor. The plant generated in this way may be referred to as a "single trait converted plant". The technique can also be used on a parental line of a hybrid.

"Progeny" as used herein refers to a plant obtained from a plant designated NUN 50215 LEL. A progeny may be obtained by regeneration of cell culture or tissue culture or parts of a plant of said variety or selfing of a plant of said variety or by producing seeds of a plant of said variety. In further embodiments, progeny may also encompass plants obtained from crossing of at least one plant of said variety with another Leek plant of the same variety or another variety or (breeding) line, or with wild Leek plants. A progeny may comprise a mutation or a transgene. A first generation progeny" or is the progeny directly derived from, obtained from, obtainable from or derivable from the parent plant by, e.g., traditional breeding methods (selfing and/or cross-pollinating) or regeneration. Thus, a plant of NUN 50215 LEL is the male parent, the female parent or both of a first generation progeny of NUN 50215 LEL. Progeny may have all the physiological and morphological characteristics of variety NUN 50215 LEL when grown under the same environmental conditions and/or progeny may have (be selected for having) one or more of the distinguishing characteristics of Leek of the invention. Using common breeding methods such as backcrossing or recurrent selection, one or more specific characteristics may be introduced into said variety, to provide or a plant comprising all but 1, 2, or 3 or more of the morphological and physiological characteristics of NUN 50215 LEL (as listed in Table 1 and/or 2)

The terms "gene converted" or "conversion plant" or "single locus converted plant" in this context refer to Leek plants which are developed by backcrossing wherein essentially all of the desired morphological and physiological characteristics of the parent variety or line are recovered, in addition to the one or more genes transferred into the parent via the backcrossing technique (optionally including reverse breeding or reverse synthesis of breeding lines) or via genetic engineering or through mutation breeding. Likewise a "Single Locus Converted (Conversion) Plant" refers to plants which are developed by plant breeding techniques comprising or consisting of mutation and/or by genetic transformation and/or by backcrossing, wherein essentially all of the desired morphological and physiological characteristics of a Leek variety are recovered in addition to the characteristics of the single locus having been transferred into the variety via the backcrossing technique. In case of a hybrid, the gene may be introduced in the male or female parental line.

"Marker" refers to a readily detectable phenotype, preferably inherited in codominant fashion (both alleles at a locus in a diploid heterozygote are readily detectable), with no environmental variance component, i.e., a heritability of 1.

"Average" refers herein to the arithmetic mean.

The term "mean" refers to the arithmetic mean of several measurements. The skilled person understands that the appearance of a plant depends to some extent on the growing conditions of said plant. Thus, the skilled person will know typical growing conditions for Leeks described herein. The mean, if not indicated otherwise within this application, refers to the arithmetic mean of measurements on at least 10 different, randomly selected plants of a variety or line.

DETAILED DESCRIPTION

The present invention relates to a plant of NUN 50215 LEL wherein a representative sample of seeds of said variety was deposited under the Budapest Treaty, with Accession number NCIMB 42794.

The present invention also relates to a seed of Leek variety, referred to as NUN 50215 LEL, wherein a representative sample of said seed was deposited under the Budapest Treaty, with Accession number NCIMB 42794.

In another aspect, the invention provides for a Leek plant part of variety NUN 50215 LEL, preferably a shaft or a leaf, a representative sample of seed from said variety has been deposited under the Budapest Treaty, with Accession number NCIMB 42794.

A seed of hybrid variety NUN 50215 LEL is obtainable by crossing the male parent of said variety with the female parent of said variety and harvesting the seeds produced on the female parent. The resultant seeds of said variety can be grown to produce plants of said variety. In one embodiment a seed or a plurality of seeds of said variety are packaged into a container of any size or type (e.g., bags, cartons, cans, etc.). The seed may be disinfected, primed and/or treated with various compounds, such as seed coatings or crop protection compounds. The seed produces a plant of NUN 50215 LEL.

Also provided is a plant of Leek variety NUN 50215 LEL, or a shaft or a leaf or other plant part thereof, produced from a seed, wherein a representative sample of said seeds has been deposited under the Budapest Treaty, with Accession Number NCIMB 42794.

Also a plant part obtained from variety NUN 50215 LEL is provided, wherein said plant part is selected from the group consisting of: a leaf, a harvested leaf, a part of a leaf, a shaft, a harvested shaft, a part of a shaft, a fruit, a harvested fruit, a part of a fruit, pollen, an ovule, a cell, a petiole, a shoot or a part thereof, a stem or a part thereof, a root or a part thereof, a root tip, a cutting, a seed, a part of a seed, seed coat or another maternal tissue which is part of a seed grown on said varieties, hypocotyl, cotyledon, a scion, a stock, a rootstock, a pistil, an anther, and a flower or a part thereof. Leaves and shafts are particularly important plant parts. In a further embodiment, the plant part obtained from variety NUN 50215 LEL is a cell, optionally a cell in a cell or tissue culture. That cell may be grown into a plant of NUN 50215 LEL. A part of a variety of the invention, i.e. NUN 50215 LEL (or of progeny NUN 50215 LEL or of a plant having all physiological and/or morphological characteristics but one, two or three which are different from those of NUN 50215 LEL) further encompasses any cells, tissues, organs obtainable from the seedlings or plants in any stage of maturity.

The invention also provides for a food or feed product or a processed product comprising or consisting of a plant part described herein wherein the plant part can be identified as a part of the plant of the invention. Preferably, the plant part is a Leek shaft or part thereof or Leek leaf or part thereof and/or an extract from a plant part described herein, each comprising at least one cell of NUN 50215 LEL. The food or feed product may be fresh or processed, e.g., dried, grinded, powdered, pickled, chopped, cooked, roasted, in a sauce, in a sandwich, pasted, puréed or concentrated, juiced, pickled, canned, steamed, boiled, fried, blanched and/or frozen, etc.

Such a plant part of NUN 50215 LEL can be stored and/or processed further. Encompassed are therefore also food or feed products comprising one or more of such parts, such as canned, chopped, cooked, roasted, in a sauce, in a sandwich, pasted, puréed or concentrated, juiced, frozen, dried, pickled, or powdered Leek parts from NUN 50215 LEL or from progeny of said varieties, or from a derived variety, such as a plant having all but one, two or three physiological and/or morphological characteristics of NUN 50215 LEL.

In a preferred embodiment, the invention provides for a Leek leaf or shaft of variety NUN 50215 LEL, or a part of a leaf or shaft of said variety. The leaf or shaft can be in any stage of maturity, for example immature or mature. In another embodiment, the invention provides for a container comprising or consisting of a plurality of harvested Leek leaves or shafts or parts thereof, or leaves or shafts of progeny thereof, or leaves or shafts of a derived variety.

In another embodiment the plant, plant part or seed of NUN 50215 LEL is inside a container. For example, containers such as cans, boxes, crates, bags, cartons, Modified Atmosphere Packaging, films (e.g. biodegradable films), etc. comprising a plant or a part of a plant (fresh and/or processed) of NUN 50215 LEL or a seed of NUN 50215 LEL are also provided herein. In a preferred embodiment, the container comprises a plurality of seeds of NUN 50215 LEL, or a plurality of plant parts of NUN 50215 LEL.

The present invention further relates to a Leek variety, referred to as NUN 50215 LEL, which—when compared to its REFERENCE VARIETY Krypton—has the following distinguishing characteristics: 1) Average plant height; 2) Shaft bulb formation type; 3) Shaft narrowing type; 4) Leaf blade bending; 5) Average leaf blade length; 6) Average leaf angle; and 7) Leaf blade color, where the characteristics are determined at the 5% significance level for plants grown under the same environmental conditions. Also encompassed by the present invention are parts of that plant.

In one embodiment a plant of NUN 50215 LEL or a progeny plant thereof, comprises all of the following morphological and/or physiological characteristics (i.e. average values of distinguishing characteristics, as indicated on the USDA Objective description of variety—Leek (unless indicated otherwise)): 1) Average plant height; 2) Shaft bulb formation type; 3) Shaft narrowing type; 4) Leaf blade bending; 5) Average leaf blade length; 6) Average leaf angle; and 7) Leaf blade color, where the characteristics are determined at the 5% significance level for plants grown under the same environmental conditions. An example of values for the distinguishing characteristics collected in a trial run according to UDSA requirements can be found in Table 1. A part of this plant is also provided.

The invention further provides a Leek plant which does not differ from the plant of NUN 50215 LEL as determined at the 1%, 2%, 3%, 4% or 5% significance level when grown under the same environmental conditions. Thus the plants are measured in the same trial. Preferably, the trial is conducted as recommended by the USDA or UPOV. The invention also comprises a part of said plant The invention also provides a tissue or cell culture comprising cells of NUN 50215 LEL. Such a tissue culture can for example be grown on plates or in liquid culture, or be frozen for long term storage. The cells of NUN 50215 LEL used to start the culture can be selected from any plant part suitable for vegetative reproduction, or in a preferred embodiment can be selected from embryos, meristems, cotyledons, hypocotyl, pollen, leaves, shaft, anthers, roots, root tips, pistil, petiole, flower, fruit, seed, stem and stalks of NUN 50215 LEL. In another preferred embodiment, the tissue culture does not contain somaclonal variation or has reduced somaclonal variation. The skilled person is familiar with methods to reduce or prevent somaclonal variation, including regular reinitiation.

In one embodiment the invention provides a Leek plant regenerated from the tissue or cell culture of NUN 50215 LEL, wherein the regenerated plant is not significantly different from NUN 50215 LEL in all, or all but one, two or three, of the physiological and morphological characteristics (determined at the 5% significance level when grown under the same environmental conditions). Optionally, the plant has one, two or three the physiological and morphological characteristics that are affected by a mutation or by transformation. In another embodiment, the invention provides a Leek plant regenerated from the tissue or cell culture of NUN 50215 LEL, wherein the plant has all of the physiological and morphological characteristics of said variety determined at the 5% significance level when grown under the same environmental conditions. In these cases, similarity or difference of a characteristic is determined by measuring the characteristics of a representative number of plants grown under the same environmental conditions, determining whether type/degree characteristics are the same or different and determining whether numerical characteristics are significantly different (determined at the 5% significance level).

A Leek according to the invention, such as NUN 50215 LEL, or its progeny, or a plant having all physiological and/or morphological characteristics but one, two or three which are different from those of NUN 50215 LEL, can also be reproduced using vegetative reproduction methods. Therefore, the invention provides for a method of producing a plant, or a part thereof, of variety NUN 50215 LEL, comprising vegetative propagation of said variety. Vegetative propagation comprises regenerating a whole plant from a plant part of variety NUN 50215 LEL (or from a progeny of said variety or from or a plant having all physiological and/or morphological characteristics of said variety but one, two or three different characteristics), such as a cutting, a cell culture or a tissue culture.

The invention also concerns methods of vegetatively propagating a part of the plant of the invention NUN 50215 LEL. In certain embodiments, the method comprises the steps of: (a) collecting tissue or cells capable of being propagated from a plant of the invention; (b) cultivating said tissue or cells to obtain proliferated shoots; and (c) rooting said proliferated shoots, to obtain rooted plantlets. Steps (b) and (c) may also be reversed, i.e. first cultivating said tissue to obtain roots and then cultivating the tissue to obtain shoots, thereby obtaining rooted plantlets. The rooted plantlets may then be further grown, to obtain plants. In one embodiment, the method further comprises step (d) growing plants from said rooted plantlets. Therefore, the method also comprises regenerating a whole plant from said part of NUN 50215 LEL.

In a preferred embodiment, the part of the plant to be propagated is is a cutting, a cell culture or a tissue culture.

The invention also provides for a vegetatively propagated plant of variety NUN 50215 LEL (or from progeny of said variety or from or a plant having all but one, two or three physiological and/or morphological characteristics of NUN 50215 LEL) wherein the plant has all of the morphological and physiological characteristics of NUN 50215 LEL when the characteristics are determined at the 5% significance level for plants grown under the same conditions. In another embodiment, the propagated plant has all but one, two or three of the morphological and physiological characteristics of NUN 50215 LEL when the characteristics are determined at the 5% significance level for plants grown under the same conditions. A part of said propagated plant or said propagated plant with one, two or three differences is also included.

In an embodiment, the invention provides a method for producing a Leek plant part, preferably a shaft or leaf, comprising the steps of:
 a. Growing a plant of NUN 50215 LEL until it develops a leaf, or until it develops a shaft
 b. Collecting the leaf or shaft of step a)

Preferably, the leaf or shaft is collected at harvest maturity. A plant of NUN 50215 LEL can be produced by seeding directly in the soil (e.g., field) or by germinating the seeds in controlled environment conditions (e.g., greenhouses) and optionally then transplanting the seedlings into the field. For example, the seed can be sown into prepared seed beds where they will remain for the entire production the crop. Leek can also be grown entirely in greenhouses In still another aspect the invention provides a method of producing a Leek plant, comprising crossing a plant of Leek NUN 50215 LEL with a second Leek plant at least once, allowing seed to develop and optionally harvesting said progeny seed. The skilled person can select progeny from said crossing. Optionally, the progeny is crossed twice, thrice, or four, five, six or seven times, and allowed to set seed. In one embodiment of the invention, the first step in "crossing" comprises planting seeds of a first and a second parent Leek plant, often in proximity so that pollination will occur; for example, mediated by insect vectors. Alternatively, pollen can be transferred manually. Where the plant is self-pollinated, pollination may occur without the need for direct human intervention other than plant cultivation. After pollination the plant can produce seed.

In yet another aspect the invention provides a method of producing a plant, comprising selfing a plant of variety NUN 50215 LEL one or more times, and selecting a progeny plant from said selfing. In one aspect the progeny plant retains all the distinguishing characteristics of NUN 50215 LEL described above. In a different embodiment the progeny plant comprises all (or all but one, two or three) of the physiological and morphological characteristic of NUN 50215 LEL of Table 1, and/or Table 2. In a further embodiment the progeny plant comprises all physiological and morphological characteristic of NUN 50215 LEL when grown under the same environmental conditions.

In other aspects, the invention provides a progeny plant of variety NUN 50215 LEL such as a progeny plant obtained by further breeding that variety. Further breeding with the variety of the invention includes selfing that variety one or more times and/or cross-pollinating that variety with another Leek plant or variety one or more times. In particular, the invention provides for a progeny plant that retains all the essential morphological and physiological characteristics of NUN 50215 LEL or, in another embodiment, a progeny plant that retains all, or all but one, two or three, of the morphological and physiological characteristics of NUN 50215 LEL, optionally all or all but one, two or three of the characteristics as listed in Table 1 and/or 2, when grown under the same environmental conditions, determined at the 5% significance level for numerical characteristics. In a preferred embodiment, the progeny is a first generation progeny, i.e. the ovule or the pollen (or both) used in the crossing is an ovule or pollen of variety NUN 50215 LEL, i.e. the pollen comes from an anther of NUN 50215 LEL and the ovule comes from an ovary of NUN 50215 LEL. In another aspect, the invention provides for a vegetative reproduction of the variety and a plant having all, or all but 1, 2, or 3 of the physiological and morphological characteristics of NUN 50215 LEL (e.g. as listed in Table 1 and/or 2).

The invention also provides a method for collecting pollen of NUN 50215 LEL, comprising the steps of:
 a. Growing a plant of NUN 50215 LEL until at least one flower develops pollen
 b. Collecting the pollen of step a)

Preferably, the pollen is collected when it is mature or ripe. A suitable method for collecting pollen comprises collecting anthers or the part of the anther that contains pollen, for example by cutting it off. Pollen can be collected in containers. Optionally, collected pollen can be used to pollinate a Leek flower.

The morphological and/or physiological differences between two different individual plants of the invention (e.g. between NUN 50215 LEL and a progeny of NUN 50215 LEL) or between a plant of NUN 50215 LEL or progeny of said variety, or a plant having all, or all but 1, 2, or 3, of the physiological and morphological characteristics of NUN 50215 LEL (or all, or all but 1, 2, or 3 of the characteristics as listed in Table 1 and/or 2) and another known variety can easily be established by growing said variety next to each other or next to the other variety (in the same field, under the same environmental conditions), preferably in several locations which are suitable for said Leek cultivation, and measuring morphological and/or physiological characteristics of a number of plants (e.g., to calculate an average value and to determine the variation range/uniformity within the variety). For example, trials can be carried out in Acampo Calif., USA (N 38 degrees 07'261"/W 121 degrees 18' 807", USA, whereby various characteristics, for example days from seeding to harvest, plant height, plant attitude, leaf shape, leaf color, leaf angle, shaft size, disease resistance, insect resistance, can be measured and directly compared for species of Leek. Thus, the invention comprises Leek plant having one, two or three physiological and/or morphological characteristics which are different from those of the plant of NUN 50215 LEL and which otherwise has all the physiological and morphological characteristics of the plant of NUN 50215 LEL, when determined at the 5% significance level for plants grown under the same environmental conditions. In a preferred embodiment, the different characteristic is affected by a mutation, optionally induced mutation, or by transformation.

The morphological and physiological characteristics (and the distinguishing characteristics) of NUN 50215 LEL are provided in the Examples, in Table 1 and/or 2. Encompassed herein is also a plant obtainable from NUN 50215 LEL (e.g. by selfing and/or crossing and/or backcrossing with said variety and/or progeny of said variety) comprising all or all but one, two or three of the physiological and morphological characteristics of NUN 50215 LEL listed in Table 1 and/or 2 as determined at the 5% significance level for numerical characteristics or identical for non-numerical characteristics when grown under the same environmental conditions and/or comprising one or more (or all; or all except one, two or three) characteristics when grown under the same environmental conditions.

Also at-harvest and/or post-harvest characteristics of leaves and shafts can be compared, such as cold storage holding quality, shaft size, and leaf waxiness can be measured using known methods.

The morphological and/or physiological characteristics may vary somewhat with variation in the environment (such as temperature, light intensity, day length, humidity, soil, fertilizer use), which is why a comparison under the same environmental conditions is preferred. Colors can best be measured against The Munsell Book of Color (Munsell Color Macbeth Division of Kollmorgan Instruments Corporation) or using the Royal Horticultural Society Chart (World Wide Web at rhs.org.uk/Plants/RHS-Publications/RHS-colour-charts).

In yet a further embodiment, the invention provides for a method of producing a new Leek plant. The method comprises crossing a plant of the invention i.e. NUN 50215 LEL, or a plant comprising all but 1, 2, or 3 of the morphological and physiological characteristics of said variety (as listed in Table 1 and/or 2), or a progeny plant thereof, either as male or as female parent, with a second Leek plant (or a wild relative of Leek) one or more times, and/or selfing a Leek plant according to the invention i.e. NUN 50215 LEL, or a progeny plant thereof, one or more times, and selecting progeny from said crossing and/or selfing. The second Leek plant may for example be a line or variety of the species *Allium ampeloprasum*, or other *Allium* species or even other Alliceae species.

The invention provides for methods of producing plants which retain all the morphological and physiological characteristics of a plant of the invention i.e. NUN 50215 LEL. The invention provides also for methods of producing a plant comprising all but 1, 2, or 3 or more of the morphological and physiological characteristics of NUN 50215 LEL (e.g. as listed in Table 1 and/or 2), but which are still genetically closely related to said variety. The relatedness can, for example be determined by fingerprinting techniques (e.g., making use of isozyme markers and/or molecular markers such as Single-nucleotide polymorphism (SNP) markers, amplified fragment length polymorphism (AFLP) markers, microsatellites, minisatellites, Random Amplified Polymorphic DNA (RAPD) markers, restriction fragment length polymorphism (RFLP) markers and others). A plant is "closely related" to NUN 50215 LEL if its DNA fingerprint is at least 80%, 90%, 95% or 98% identical to the fingerprint of NUN 50215 LEL. In a preferred embodiment AFLP markers are used for DNA fingerprinting (Vos et al. 1995, Nucleic Acid Research 23: 4407-4414). A closely related plant may have a Jaccard's Similarity index of at least about 0.8, preferably at least about 0.9, 0.95, 0.98 or more (Parvathaneni et al., J. Crop Sci. Biotech. 2011 (March) 14 (1): 39-43).

The invention also provides a plant and a variety obtained or selected by applying these methods on NUN 50215 LEL. Such a plant may be produced by crossing and/or selfing, or alternatively, a plant may simply be identified and selected amongst plants of said variety, or progeny of said variety, e.g. by identifying a variant within NUN 50215 LEL or within progeny of said variety (e.g. produced by selfing) which variant differs from NUN 50215 LEL in one, two or three of the morphological and/or physiological characteristics (e.g. in one, two or three distinguishing characteristics), e.g. those listed in Table 1 and/or 2 or others. In one embodiment the invention provides a Leek plant having a Jaccard's Similarity index with NUN 50215 LEL of at least 0.8, e.g. at least 0.85, 0.9, 0.95, 0.98 or even at least 0.99.

WO2013182646, which is incorporated by reference, relates to a non-destructive method for analyzing maternal DNA of a seed. In this method the DNA is dislodged from the seed coat surface and can be used to collect information on the genome of the maternal parent of the seed. This method for analyzing maternal DNA of a seed comprises the steps of contacting a seed with a fluid to dislodge DNA from the seed coat surface, and analyzing the DNA thus dislodged from the seed coat surface using methods known in the art. The skilled person is thus able to determine whether a seed has grown on a plant of a plant of the invention i.e. NUN 50215 LEL is a progeny of said variety, because the seed coat of the seed is a maternal tissue genetically identical to NUN 50215 LEL. In one embodiment, the present invention relates to a seed coat comprising maternal tissue of NUN 50215 LEL. In another embodiment the invention relates to a Leek seed comprising a maternal tissue of NUN 50215 LEL.

By crossing and/or selfing also (one or more) single traits may be introduced into the variety of the invention i.e. NUN 50215 LEL (e.g., using backcrossing breeding schemes), while retaining the remaining morphological and physiological characteristics of said variety and/or while retaining one or more or all distinguishing characteristics. A single trait converted plant may thereby be produced. For example, disease resistance genes may be introduced, genes responsible for one or more quality traits, yield, etc. Both single genes (e.g. dominant or recessive) and one or more QTLs (quantitative trait loci) may be transferred into NUN 50215 LEL by breeding with said variety.

Alternatively, a single trait converted plant or single locus converted plant of NUN 50215 LEL may be produced by the following steps
   a. obtaining a cell or tissue culture of cells of NUN 50215 LEL;
   b. genetically transforming or mutating said cells;
   c. growing the cells into a plant; and
   d. optionally selecting a plant that contains the desired single locus conversion The skilled person is familiar with various techniques for genetically transforming a single locus in a plant cell, or mutating said cells.

Any trait may be introduced into a plant according to the invention, i.e. NUN 50215 LEL, progeny of said variety or into a plant comprising all but 1, 2, or 3 or more of the morphological and physiological characteristics of NUN 50215 LEL (e.g. as listed in Table 1). Resistance to one or more of the following diseases or pests is preferably introduced into plants of the invention: Aphid resistance, Pickle Worm, Darkling Ground Beetle, Banded Cucumber Beetle, Mite, Western Spotted Cucumber Beetle, Leek Leafhopper, Leek Worm, Western Striped Cucumber Beetle or Leek Leafminer, *Thrips tabaci*, Leek moth and Onion fly. Other resistance genes, against pathogenic viruses, fungi, bacteria, nematodes, insects or other pests may also be introduced.

Thus, invention also provides a method for developing a Leek plant in a Leek breeding program, using a Leek plant of the invention, or its parts as a source of plant breeding material. Suitable plant breeding techniques are recurrent selection, backcrossing, pedigree breeding, mass selection, mutation breeding and/or genetic marker enhanced selection. For example, in one aspect, the method comprises crossing NUN 50215 LEL or progeny of said variety, or a plant comprising all but 1, 2, or 3 or more of the morphological and physiological characteristics of NUN 50215 LEL (e.g. as listed in Table 1 and/or 2), with a different Leek plant, and wherein one or more offspring of the crossing are subject to one or more plant breeding techniques selected from the group consisting of recurrent selection, backcrossing, pedigree breeding, mass selection, mutation breeding and genetic marker enhanced selection (see e.g. Brotman et al., Theor Appl Genet (2002) 104:1055-1063). For breeding methods in general see Principles of Plant Genetics and Breeding, 2007, George Acquaah, Blackwell Publishing, ISBN-13: 978-1-4051-3646-4.

The invention also provides a Leek plant comprising at least a first set of the chromosomes of Leek variety NUN 50215 LEL, a sample of seed of said variety having been deposited under Accession Number NCIMB 42794; optionally further comprising a single locus conversion or a mutation, wherein said plant has essentially all of the morphological and physiological characteristics of the plant comprising at least a first set of the chromosomes of said variety. In another embodiment, this single locus conversion confers a trait selected from the group consisting of yield, storage properties, color, male sterility, herbicide tolerance, insect resistance, pest resistance, disease resistance, environmental stress tolerance, modified carbohydrate metabolism and modified protein metabolism.

In one embodiment, a plant according to the invention, i.e. NUN 50215 LEL may also be mutated (by e.g. irradiation, chemical mutagenesis, heat treatment, etc.) and mutated seeds or plants may be selected in order to change one or more characteristics of said variety. Methods such as TILLING may be applied to Leek populations in order to identify mutants. Similarly, NUN 50215 LEL may be transformed and regenerated, whereby one or more chimeric genes are introduced into the variety or into a plant comprising all but 1, 2, 3, or more of the morphological and physiological characteristics (e.g. as listed in Table 1 and/or 2). Transformation can be carried out using standard methods, such as *Agrobacterium tumefaciens* mediated transformation or biolistics, followed by selection of the transformed cells and regeneration into plants. A desired trait (e.g. genes conferring pest or disease resistance, herbicide, fungicide or insecticide tolerance, etc.) can be introduced into NUN 50215 LEL, or progeny of said variety, by transforming said variety or progeny of said variety with a transgene that confers the desired trait, wherein the transformed plant retains all or all but one, two or three of the phenotypic and/or morphological and/or physiological characteristics of NUN 50215 LEL or the progeny of said variety and contains the desired trait.

The invention also provides a plant or a cell of a plant comprising a desired trait produced by mutating a plant of variety NUN 50215 LEL or a cell thereof and selecting a plant the desired trait, wherein the mutated plant retains all or all but one of the phenotypic and morphological characteristics of said variety, optionally as described for each variety in in Table 1 and/or 2, and contains the desired trait and wherein a representative sample of seed of variety NUN 50215 LEL has been deposited under Accession Number NCIMB 42794. In a further embodiment, the desired trait is selected from the group consisting of yield, herbicide tolerance, insect resistance, pest resistance, disease resistance, Alternaria resistance, Rust resistance, Purple blotch resistance, male sterility, environmental stress tolerance, modified carbohydrate metabolism, modified protein metabolism and ripening.

A suitable method for inducing mutation in NUN 50215 LEL comprises the steps of:
   a. Exposing a seed, a plant or a plant part or a cell of NUN 50215 LEL to a mutagenic compound or to radiation, wherein a representative sample of seed of NUN 50215 LEL is deposited under Accession Number NCIMB 42794,
   b. Selecting a seed, a plant or a plant part or a cell of NUN 50215 LEL having a mutation
   c. Optionally growing and/or multiplying the seed, plant or plant part or cell of NUN 50215 LEL having the mutation.

The invention also provides a plant having one, two or three physiological and/or morphological characteristics which are different from those of NUN 50215 LEL and which otherwise has all the physiological and morphological characteristics of said variety, wherein a representative sample of seed of variety NUN 50215 LEL has been deposited under Accession Number NCIMB 42794. In particular variants which differ from NUN 50215 LEL in none, one, two or three of the characteristics mentioned in Table 1 and/or 2 are encompassed.

A part of a variety of the invention, i.e. NUN 50215 LEL (or of progeny of said varieties or of a plant having all physiological and/or morphological characteristics but one, two or three which are different from those of said variety) encompasses any cells, tissues, organs obtainable from the seedlings or plants, such as but not limited to: a Leek leaf or shaft or a part thereof, a cutting, hypocotyl, cotyledon, seed coat, pollen and the like. Such parts can be stored and/or processed further. Encompassed are therefore also food or feed products comprising a part of NUN 50215 LEL or a part of progeny of said varieties, or a part of a plant having all but one, two or three physiological and/or morphological characteristics of NUN 50215 LEL, comprising one or more of such parts, optionally processed (such as canned, chopped, cooked, roasted, in a sauce, in a sandwich, pasted, puréed or concentrated, juiced, frozen, dried, pickled, or powdered).

In one aspect a haploid plant and/or a doubled haploid plant of NUN 50215 LEL, or of a plant having all but one, two or three physiological and/or morphological characteristics of NUN 50215 LEL, or progeny of any of these, is encompassed herein. Haploid and doubled haploid (DH) plants can, for example, be produced by cell or tissue culture and chromosome doubling agents and regeneration into a whole plant. For DH production chromosome doubling may be induced using known methods, such as colchicine treatment or the like.

In yet another aspect haploid plants and/or doubled haploid plants derived from NUN 50215 LEL that, when combined, make a set of parents of NUN 50215 LEL are encompassed herein. Thus the haploid plant and/or the doubled haploid plant of NUN 50215 LEL can be used in a method for generating parental lines of NUN 50215 LEL.

Using methods known in the art like "reverse synthesis of breeding lines" or "reverse breeding", it is possible to produce parental lines for a hybrid plant such as NUN 50215 LEL; where normally the hybrid is produced from the parental lines. Thus, this method introduces a tool that was not available in traditional breeding: a skilled person can take any individual heterozygous plant (called a "phenotypically superior plant" in Example 2 of WO2014076249; NUN 50215 LEL is such a plant) and generate a combination of parental lines (reverse breeding parental lines) that, when crossed, produce the variety NUN 50215 LEL. It is not necessary that the reverse breeding parental lines are identical to the original parental lines. Such new breeding methods are based on the segregation of individual alleles in the spores produced by a desired plant and/or in the progeny derived from the self-pollination of that desired plant, and on the subsequent identification of suitable progeny plants in one generation, or in a limited number of inbred cycles. Such a method is known from WO2014076249 or from Wijnker et al., Nature Protocols Volume: 9, Pages: 761-772 (2014) DOI: doi:10.1038/nprot.2014.049, which are enclosed by reference. Such method for producing parental lines for a hybrid organism, comprises the steps of: a) defining a set of genetic markers that are present in a heterozygous form (H) in a partially heterozygous starting organism; b) producing doubled haploid lines from spores of the starting organism: c) genetically characterizing the doubled haploid lines thus obtained for the said set of genetic markers to determine whether they are present in a first homozygous form (A) or in a second homozygous form (B); d) selecting at least one pair of doubled haploid lines that have complementary alleles for at least a subset of the genetic markers, wherein each member of the pair is suitable as a parental line for a hybrid organism.

Thus in one aspect, the invention relates to a method of producing a combination of parental lines of a plant of the invention (NUN 50215 LEL) comprising the step of making doubled haploid cells from haploid cells from said plant or a seed of that plant; and optionally crossing these parental lines to produce and collect seeds. In another aspect, the invention relates to a combination of parental lines produced by this method. In still another aspect said combination of parental lines can be used to produce a seed or plant of NUN 50215 LEL when these parental lines are crossed. In still another aspect, the invention relates to a combination of parental lines from which a seed or plant having all physiological and/or morphological characteristics of NUN 50215 LEL (when the characteristics are determined at the 5% significance level for plants grown under the same conditions).

In another aspect, the invention comprises a method for making doubled haploid cells from haploid cells of NUN 50215 LEL according to various methods known to the skilled person. A suitable method is colchicine treatment.

In another alternative aspect, the invention provides a method of introducing a single locus conversion or single trait conversion or a desired trait into NUN 50215 LEL comprising:

a. obtain a combination of a parental lines of NUN 50215 LEL, optionally through reverse synthesis of breeding lines, b. introduce a single locus conversion in at least one of the parents of step a;

c. crossing the converted parent with the other parent of step a to obtain seed of NUN 50215 LEL A combination of a male and a female parental line of NUN 50215 LEL can be generated by methods described herein, for example through reverse synthesis of breeding lines.

In an embodiment of the invention, Step b) of the above method—introduce a single locus conversion in at least one of the parents of step a—may be done through the following method:

i. obtaining a cell or tissue culture of cells of the parental line of NUN 50215 LEL;

ii. genetically transforming or mutating said cells;

iii. growing the cells into a plant; and iv. optionally selecting plants that contain the single locus conversion, the single trait conversion or the desired trait.

In another embodiment of the invention, Step b) of the above method—introduce a single locus conversion in at least one of the parents of step a—may also be done through the following method:

i. crossing the parental line of NUN 50215 LEL with a second Leek plant comprising the single locus conversion, the single trait conversion or the desired trait;

ii. selecting F1progeny plants that contain the single locus conversion, the single trait conversion or the desired trait;

iii. crossing said selected progeny plants of step ii with the parental line of step i, to produce a backcross progeny plant;

iv. selecting backcross progeny plants comprising the single locus conversion, the single trait conversion or the desired trait and otherwise all or all but one, two or three of the morphological and physiological characteristics the parental line of step i to produce selected backcross progeny plants; and v. optionally repeating steps iii and iv one or more times in succession to produce selected second, third or fourth or higher backcross progeny plants comprising the single locus conversion, the single trait conversion or the desired trait and otherwise all or all but one, two or three of the morphological and physiological characteristics the parental line of step i to produce selected backcross progeny plants, when grown in the same environmental conditions.

The invention further relates to plants obtained by this method.

The above method is provided, wherein the single locus conversion concerns a trait, wherein the trait is yield or pest resistance or disease resistance. In one embodiment the trait is disease resistance and the resistance is conferred to Aphid resistance, Pickle Worm, Darkling Ground Beetle, Banded Cucumber Beetle, Mite, Western Spotted Cucumber Beetle, Leek Leafhopper, Leek Worm, Western Striped Cucumber Beetle or Leek Leafminer, *Thrips tabaci*, Leek moth and Onion fly. Other resistance genes, against pathogenic viruses, fungi, bacteria, nematodes, insects or other pests may also be introduced.

Thus, the invention also provides a combination of parental lines which, when crossed, produce a seed or plant having all physiological and/or morphological characteristics of NUN 50215 LEL but one, two or three which are different (when grown under the same environmental conditions), as well as a seed or plant having all physiological and/or morphological characteristics of NUN 50215 LEL but one, two or three which are different (when the characteristics are determined at the 5% significance level for plants grown under the same conditions).

Also provided is a plant part obtainable from variety NUN 50215 LEL or from progeny of said variety or from a plant having all but one, two or three physiological and/or morphological characteristics which are different from those of NUN 50215 LEL, or from a vegetatively propagated plant of NUN 50215 LEL (or from its progeny or from a plant having all or all but one, two or three physiological and/or morphological characteristics which are different from those of NUN 50215 LEL), being selected from the group consisting of a leaf, a harvested leaf, a part of a leaf, a shaft, a harvested shaft, a part of a shaft, a fruit, a harvested fruit, a part of a fruit, a leaf, a part of a leaf, pollen, an ovule, a cell, a petiole, a shoot or a part thereof, a stem or a part thereof, a root or a part thereof, a root tip, a cutting, a seed, a part of a seed, seed-coat or another maternal tissue which is part of a seed grown on NUN 50215 LEL, or hypocotyl, cotyledon, a scion, a stock, a rootstock, a pistil, an anther, and a flower or a part thereof.

In still yet another aspect, the invention provides a method of determining the genotype of a plant of the invention comprising the step of detecting in the genome (e.g., a sample of nucleic acids) of the plant at least a first polymorphism or an allele. The skilled person is familiar with many suitable methods of genotyping, detecting a polymorphism or detecting an allele including restriction fragment length polymorphism identification (RFLP) of genomic DNA, random amplified polymorphic detection (RAPD) of genomic DNA, amplified fragment length polymorphism detection (AFLP), polymerase chain reaction (PCR), DNA sequencing, allele specific oligonucleotide (ASO) probes, and hybridization to DNA microarrays or beads. Alternatively, the entire genome could be sequenced. The method may, in certain embodiments, comprise detecting a plurality of polymorphisms in the genome of the plant, for example by obtaining a sample of nucleic acid from a plant and detecting in said nucleic acids a plurality of polymorphisms. The method may further comprise storing the results of the step of detecting the plurality of polymorphisms on a computer readable medium Marketable Leek leaves and shafts are generally sorted by size and quality after harvest. Alternatively the Leek leaves and shafts can be sorted by color or after-harvest treatments.

All documents (e.g., patent publications) are herein incorporated by reference in their entirety.

CITED REFERENCES

WO2013182646
WO2014076249
Brotman et al., Theor Appl Genet (2002) 104:1055-1063

Colijn-Hooymans (1994), Plant Cell, Tissue and Organ Culture 39: 211-2177)
Parvathaneni et al., J. Crop Sci. Biotech. 2011 (March) 14 (1): 39~43
Ren et al., In Vitro Cell.Dev.Biol.-Plant (2013) 49:223-229
Vos et al. 1995, Nucleic Acid Research 23: 4407-4414
Wijnker et al., Nature Protocols Volume: 9, Pages: 761-772 (2014) DOI: doi:10.1038/nprot.2014.049
"Guidelines for the Conduct of Tests for Distinctness, Uniformity and Stability, TG/85/7 (UPOV, Geneva 2008); world wide web at upov.int/edocs/tgdocs/en/tg085.pdf.

Examples

Development of NUN 50215 LEL

The hybrid NUN 50215 LEL was developed from a male and female proprietary inbred line of Nunhems. The female and male parents were crossed to produce hybrid (F1) seeds of NUN 50215 LEL The seeds of NUN 50215 LEL can be grown to produce hybrid plants and parts thereof (e.g. Leek leaves and shafts). The hybrid NUN 50215 LEL can be propagated by seeds or vegetative.

The hybrid variety is uniform and genetically stable. This has been established through evaluation of horticultural characteristics. Several hybrid seed production events resulted in no observable deviation in genetic stability. Coupled with the confirmation of genetic stability of the female and male parents the Applicant has concluded that NUN 50215 LEL is uniform and stable.

Deposit Information

A total of 2500 seeds of the hybrid variety NUN 50215 LEL will be deposited according to the Budapest Treaty by Nunhems B. V. on 26 Jul. 2017, at the NCIMB Ltd., Ferguson Building, Craibstone Estate, Bucksburn, Aberdeen AB21 9YA, United Kingdom (NCIMB). The deposit will be assigned NCIMB number 42794. A deposit of NUN 50215 LEL and of the male and female parent line is also maintained at Nunhems B. V.

Access to the deposits will be available during the pendency of this application to persons determined by the Director of the U.S. Patent Office to be entitled thereto upon request. Subject to 37 C.F.R. § 1.808(b), all restrictions imposed by the depositor on the availability to the public of the deposited material will be irrevocably removed upon the granting of the patent. The deposit will be maintained for a period of 30 years, or 5 years after the most recent request, or for the enforceable life of the patent whichever is longer, and will be replaced if it ever becomes nonviable during that period. Applicant does not waive any rights granted under this patent on this application or under the Plant Variety Protection Act (7 USC 2321 et seq.).

The most similar variety to NUN 50215 LEL is referred to as Reference Variety, a variety from Nunhems with the commercial name Krypton. In Table 1 a comparison between NUN 50215 LEL and the Reference Variety will be shown based on a trial in the USA during the trial season 2018. Trial location Acampo, Calif., USA (N38.192873, W121.232637). Transplanting date for NUN 50215 LEL and REFERENCE VARIETY: 25 Oct. 2017.

A trial of 40 plants of each variety, from which at least 15 plants or plant parts were randomly selected, will be used to measure characteristics. For numerical characteristics averages will be calculated. For non-numerical characteristics the type/degree will be determined. In Table 1 the USDA descriptors of NUN 50215 LEL (this application) and the Reference Variety (commercial variety) are listed, which will be measured in the trial to be performed.

In accordance with one aspect of the present invention, there is provided a plant having the physiological and morphological characteristics of NUN 50215 LEL as will be presented in Table 1.

TABLE 1

Objective description of varieties NUN 50215 LEL and Reference Variety

| Descriptor | Application Variety NUN 50215 LEL | Reference Variety Krypton |
|---|---|---|
| 1. Harvest time | | |
| Days from seeding to harvest | | |
| 2. Plant | | |
| Plant height in cm | 45.51 | 41.83 |
| Plant length in cm (at harvest) | 50.77 | 48.98 |
| Foliage attitude: 1 = erect (Reese); 2 = semi-erect (Linex); 3 = horizontal (De Carentan 2) | 2 | 2 |
| 3. Shaft (Column) | | |
| Shaft length (base of plant above roots to divergence of the 1$^{st}$ non-senescing leaf) in cm | 7.25 | 7.93 |
| Shaft diameter in mm | 2.61 | 2.71 |
| Shaft ratio length/diameter | 2.78 | 2.93 |
| Shaft bulb formation: 1 = absent or very weak; 2 = weak; 3 = medium; 4 = strong; 5 = very strong | 2 | 1 |
| Shaft narrowing towards the base: 1 = absent; 2 = present | 1 | 2 |
| 4. Leaf blade | | |
| Leaf blade bending: 1 = strong (Blauwgroene winter); 2 = medium (Flextan); 3 = weak (Bell) | 2 | 3 |
| Leaf blade length in cm | 44.19 | 41.11 |
| Leaf blade width in cm | 3.96 | 4.24 |
| Leaf angle (degrees from column) | 58.8 | 49.33 |
| Leaf blade color: 1 = yellow green (Jaune gros du Poitou); 2 = green (Premier); 3 = gray green (Zwitserse Reuzen); blue green (Blauwgroene Winter) | 4 | 3 |
| Leaf blade color intensity: 1 = light; 2 = medium; 3 = dark | 2 | 2 |
| Leaf blade anthocyanin coloration: 1 = absent or very weak; 2 = weak; 3 = medium; 4 = strong; 5 = very strong | 1 | 1 |
| Leaf blade waxiness: 1 = absent or very weak (Kingston); 2 = weak (Carlton); 3 = medium (Linx); 4 = strong (Flextan); 5 = very strong | 3 | 3 |

Table 1 contains typical values. Values may vary due to environment. Other values that are substantially equivalent are also within the scope of the invention. N.A.=not applicable; n.r.=not recorded.

What is claimed is:

1. A plant, a plant part or a seed of Leek variety NUN 50215 LEL, wherein a representative sample of seed of said variety is deposited under Accession Number NCIMB 42794.

2. The plant part of claim 1, wherein said plant part is a leaf, a shaft, a pollen, an ovule, a fruit, a cutting, a flower, or a cell.

3. A seed that produces the plant of claim 1.

4. A seed grown on the plant of claim 1.

5. A tissue or cell culture comprising cells of the plant of claim 1.

6. The tissue or cell culture according to claim 5, comprising cells or protoplasts obtained from said plant part of said Leek variety NUN 50215 LEL, wherein said plant part is an embryo, a meristem, a cotyledon, a hypocotyl, a pollen, a leaf, an anther, a root, a root tip, a pistil, a petiole, a flower, a fruit, a shaft, a seed, a stem or a stalk.

7. A Leek plant regenerated from the tissue or cell culture of claim 5 or claim 6, wherein the regenerated Leek plant has all of the physiological and morphological characteristics of the Leek plant of variety NUN 50215 LEL when grown under the same environmental conditions, and wherein a representative sample of seed of Leek variety NUN 50215 LEL is deposited under Accession Number NCIMB 42794.

8. A method of producing the plant of claim 1, comprising vegetative propagation of said plant part of Leek variety NUN 50215 LEL, wherein a representative sample of seed of said Leek variety is deposited under Accession Number NCIMB 42794.

9. The method of claim 8, wherein said vegetative propagation comprises regenerating a Leek plant from said plant part of said leek variety NUN 50215 LEL, wherein the regenerated Leek plant has all of the physiological and morphological characteristics of the Leek plant of variety NUN 50215 LEL when grown under the same environmental conditions, and wherein a representative sample of seed of said Leek variety is deposited under Accession Number NCIMB 42794.

10. The method of claim 8, wherein said plant part is a cutting, a cell culture or a tissue culture.

11. A vegetative propagated plant or a plant part thereof of claim 1, having all of the physiological and morphological characteristics of the plant of NUN 50215 LEL when grown under the same environmental conditions, and wherein a representative sample of seed of Leek variety NUN 50215 LEL is deposited under Accession Number NCIMB 42794.

12. A method of producing a Leek progeny plant, comprising crossing the Leek plant of claim 1 with a second Leek plant at least once to produce progeny Leek plants, allowing the progeny Leek plants to form seed and selecting a progeny Leek plant from said crossing, wherein said selected progeny Leek plant has all of the physiological and morphological characteristics of the plant of NUN 50215 LEL when grown under the same environmental conditions, and wherein a representative sample of seed of Leek variety NUN 50215 LEL is deposited under Accession Number NCIMB 42794.

13. A first generation progeny plant of the plant of claim 1 obtained by selfing Leek variety NUN 50215 LEL, or cross-pollinating Leek variety NUN 50215 LEL with another Leek plant, wherein said progeny plant has all of the physiological and morphological characteristics of the plant of Leek variety NUN 50215 LEL when grown under the same environmental conditions, and wherein a representative sample of seed of said Leek variety is deposited under Accession Number NCIMB 42794.

14. A food or feed product comprising the plant part of claim 2.

15. A leek plant comprising at least a first set of the chromosomes of the plant of leek variety NUN 50215 LEL, wherein a representative sample of seed of said variety has been deposited under Accession Number NCIMB 42794, and wherein said leek plant comprising the first set of the chromosomes has all of the physiological and morphological characteristics of said leek variety NUN 50215 LEL.

16. A plant of leek variety NUN 50215 LEL, further comprising a single locus conversion, wherein a representative sample of seed of said leek variety NUN 50215 LEL has been deposited under Accession Number NCIMB 42794, and wherein said leek plant having all the physiological and morphological characteristics of said leek variety NUN 50215 LEL when grown under the same environmental conditions.

17. The plant of claim 16, wherein the single locus conversion confers trait of male sterility, herbicide tolerance, insect resistance, pest resistance, disease resistance, environmental stress tolerance, modified carbohydrate metabolism or modified protein metabolism.

18. A method of producing a leek plant having a desired trait, wherein the method comprises mutating a leek plant of variety NUN 50215 LEL and selecting a mutated leek plant with the desired trait, wherein the mutated leek plant retains all of the morphological and physiological characteristics of the leek plant of variety NUN 50215 LEL and additionally contains the desired trait, and wherein the representative sample of seed of said leek variety NUN 50215 LEL has been deposited under Accession Number NCIMB 42794.

19. The method of claim 18, wherein the desired trait is male sterility, herbicide tolerance, insect resistance, pest resistance, disease resistance, environmental stress tolerance, modified carbohydrate metabolism or modified protein metabolism.

* * * * *